(12) United States Patent
Inouye et al.

(10) Patent No.: US 11,432,809 B2
(45) Date of Patent: Sep. 6, 2022

(54) OCCLUSIVE MEDICAL DEVICE WITH FABRIC RETENTION BARB

(71) Applicant: BOSTON SCIENTIFIC SCIMED, INC., Maple Grove, MN (US)

(72) Inventors: Joshua Mark Inouye, Maple Grove, MN (US); Brian Joseph Tischler, Shoreview, MN (US); Dennis A Peiffer, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 330 days.

(21) Appl. No.: 15/965,120

(22) Filed: Apr. 27, 2018

(65) Prior Publication Data

US 2018/0310925 A1    Nov. 1, 2018

Related U.S. Application Data

(60) Provisional application No. 62/490,657, filed on Apr. 27, 2017.

(51) Int. Cl.
*A61B 17/00* (2006.01)
*A61B 17/12* (2006.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC ........ A61B 17/12022; A61B 17/12145; A61B 17/1215; A61B 17/12172;
(Continued)

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| WO | 9313712 A1 | 7/1993 |
| WO | 9504132 A1 | 2/1995 |

(Continued)

OTHER PUBLICATIONS

International Search Report and Written Opinion from PCT/US2004/008109 dated Aug. 3, 2004.

(Continued)

*Primary Examiner* — Todd J Scherbel
(74) *Attorney, Agent, or Firm* — Seager, Tufte & Wickhem LLP

(57) ABSTRACT

An occlusive implant system may include a catheter having a lumen extending from a proximal opening to a distal opening, a core wire slidably disposed within the lumen, and an occlusive implant having an expandable framework configured to shift between a collapsed configuration and an expanded configuration, and an occlusive element disposed on the expandable framework. The expandable framework may include a plurality of anchor members extending radially outward from the expandable framework, at least some of the plurality of anchor members each have a barb projecting circumferentially therefrom. The occlusive implant may be releasably connected to a distal portion of the core wire.

18 Claims, 12 Drawing Sheets

(52) U.S. Cl.
CPC .. *A61B 17/12172* (2013.01); *A61B 17/12177* (2013.01); *A61B 2017/00243* (2013.01); *A61B 2017/00526* (2013.01); *A61B 2017/00579* (2013.01); *A61B 2017/00592* (2013.01); *A61B 2017/00623* (2013.01); *A61B 2017/00632* (2013.01); *A61B 2017/00867* (2013.01); *A61B 2017/00884* (2013.01); *A61B 2017/00893* (2013.01); *A61B 2017/12095* (2013.01)

(58) Field of Classification Search
CPC .......... A61B 17/12177; A61B 17/0057; A61B 17/00579; A61B 2017/1205; A61B 2017/00592
See application file for complete search history.

(56) References Cited

U.S. PATENT DOCUMENTS

| | | |
|---|---|---|
| 3,402,710 A | 9/1968 | Maurice |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,175,545 A | 11/1979 | Termanini |
| 4,309,776 A | 1/1982 | Berguer |
| 4,341,218 A | 7/1982 | Ü |
| 4,425,908 A | 1/1984 | Simon |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,683,411 A | 11/1997 | Kavteladze et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |

(56) References Cited

U.S. PATENT DOCUMENTS

| | | |
|---|---|---|
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muij Van de Moer et al. |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 * | 5/2001 | Frazier ............ A61B 17/12122 604/500 |
| 6,231,589 B1 | 5/2001 | Wessman et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,776 B1 | 7/2001 | O'Connell |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,468,301 B1 | 10/2002 | Amplatz et al. |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,589,251 B2 | 7/2003 | Yee et al. |
| 6,599,308 B2 | 7/2003 | Amplatz |
| 6,623,508 B2 | 9/2003 | Shaw et al. |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,726,701 B2 | 4/2004 | Gilson et al. |
| 6,730,108 B2 | 5/2004 | Van Tassel et al. |

(56) References Cited

U.S. PATENT DOCUMENTS

| | | |
|---|---|---|
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,949,113 B2 | 9/2005 | Van Tassel et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,044,134 B2 | 5/2006 | Khairkhahan et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,713,282 B2 | 5/2010 | Frazier et al. |
| 7,722,641 B2 | 5/2010 | van der Burg et al. |
| 7,799,049 B2 | 9/2010 | Ostrovsky et al. |
| 8,043,329 B2 | 10/2011 | Khairkhahan et al. |
| 8,080,032 B2 | 12/2011 | van der Burg et al. |
| 8,287,563 B2 | 10/2012 | Khairkhahan et al. |
| 8,323,309 B2 | 12/2012 | Khairkhahan et al. |
| 8,663,273 B2 | 3/2014 | Khairkhahan et al. |
| 8,685,055 B2 | 4/2014 | VanTassel et al. |
| 9,943,299 B2 | 4/2018 | Khairkhahan et al. |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0220610 A1 | 11/2004 | Kreidler et al. |
| 2004/0230222 A1 | 11/2004 | van der Burg et al. |
| 2005/0203568 A1 | 9/2005 | Burg et al. |
| 2012/0172927 A1 | 7/2012 | Campbell et al. |
| 2014/0005714 A1* | 1/2014 | Quick .................. A61L 31/022 606/200 |
| 2014/0018841 A1 | 1/2014 | Peiffer et al. |
| 2014/0100596 A1 | 4/2014 | Rudman et al. |
| 2014/0148842 A1 | 5/2014 | Khairkhahan et al. |
| 2015/0080903 A1* | 3/2015 | Dillard ..................... A61F 2/01 606/110 |
| 2015/0196300 A1 | 7/2015 | Tischler et al. |

FOREIGN PATENT DOCUMENTS

| | | |
|---|---|---|
| WO | 9522359 A1 | 8/1995 |
| WO | 9601591 A1 | 1/1996 |
| WO | 9640356 A1 | 12/1996 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0108743 A1 | 2/2001 |
| WO | 0115629 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A1 | 3/2002 |
| WO | 02071977 A1 | 9/2002 |
| WO | 03007825 A1 | 1/2003 |
| WO | 03008030 A1 | 1/2003 |
| WO | 03032818 A1 | 4/2003 |
| WO | 2010081033 A1 | 7/2010 |
| WO | 2013159065 A1 | 10/2013 |

OTHER PUBLICATIONS

PCT Search Report for co-pending Application PCT/US99/26325 dated Feb. 15, 2000.

PCT Search Report from co-pending Application PCT/US02/33808 dated May 20, 2003.

Written Opinion for co-pending PCT/US/02/33808 dated Nov. 17, 2003.

International Search Report and Written Opinion dated Aug. 21, 2018 for International Application No. PCT/US2018/029684.

* cited by examiner

OCCLUSIVE MEDICAL DEVICE WITH FABRIC RETENTION BARB

CROSS-REFERENCE TO RELATED APPLICATIONS

This application claims the benefit of priority under 35 U.S.C. § 119 to U.S. Provisional Application Ser. No. 62/490,657, filed Apr. 27, 2017, the entirety of which is incorporated herein by reference.

TECHNICAL FIELD

The disclosure relates generally to percutaneous medical devices and more particularly to percutaneous occlusive medical devices for implantation into the left atrial appendage (LAA) of a heart.

BACKGROUND

Atrial fibrillation (AF) a common sustained cardiac arrhythmia affecting over 5.5 million people worldwide. Atrial fibrillation is the irregular, chaotic beating of the upper chambers of the heart. Electrical impulses discharge so rapidly that the atrial muscle quivers, or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

A continuing need exists for improved medical devices and methods to control thrombus formation within the left atrial appendage of patients suffering from atrial fibrillation.

SUMMARY

In a first aspect, an occlusive implant may comprise an expandable framework configured to shift between a collapsed configuration and an expanded configuration, and an occlusive element disposed on the expandable framework. The expandable framework may include a plurality of anchor members extending radially outward from the expandable framework. At least some of the plurality of anchor members may each have a barb projecting circumferentially therefrom.

In addition or alternatively, and in a second aspect, each of the plurality of anchor members includes a body portion and a tip portion.

In addition or alternatively, and in a third aspect, the barb projecting circumferentially from at least some of the plurality of anchor members projects from the body portion of its respective anchor member.

In addition or alternatively, and in a fourth aspect, the body portion of each anchor member is attached to the expandable framework at a base of its respective anchor member.

In addition or alternatively, and in a fifth aspect, each barb includes a forward surface facing towards the tip portion of its respective anchor member, and a rear surface facing towards the base of its respective anchor member.

In addition or alternatively, and in a sixth aspect, the rear surface is positioned at an obtuse angle to the body portion.

In addition or alternatively, and in a seventh aspect, the forward surface is positioned at an obtuse angle to the body portion.

In addition or alternatively, and in an eighth aspect, an intersection of the forward surface with the rear surface forms a barb tip, the barb tip being rounded.

In addition or alternatively, and in a ninth aspect, each barb comprises a semi-elliptical nub.

In addition or alternatively, and in a tenth aspect, the expandable framework and the plurality of anchor members are formed from a unitary tubular member.

In addition or alternatively, and in an eleventh aspect, an occlusive implant system may comprise a catheter having a lumen extending from a proximal opening to a distal opening, a core wire slidably disposed within the lumen, and an occlusive implant having an expandable framework configured to shift between a collapsed configuration and an expanded configuration and an occlusive element disposed on the expandable framework. The expandable framework may include a plurality of anchor members extending radially outward from the expandable framework. At least some of the plurality of anchor members may each have a barb projecting circumferentially therefrom. The occlusive implant may be releasably connected to a distal portion of the core wire.

In addition or alternatively, and in a twelfth aspect, the occlusive implant is disposed within the lumen proximate the distal opening in the collapsed configuration.

In addition or alternatively, and in a thirteenth aspect, a tip portion of each of the plurality of anchor members extends towards a proximal end of the occlusive implant.

In addition or alternatively, and in a fourteenth aspect, the occlusive element extends distally past all of the plurality of anchor members.

In addition or alternatively, and in a fifteenth aspect, the plurality of anchor members each extend through the occlusive element.

In addition or alternatively, and in a sixteenth aspect, an occlusive implant may comprise an expandable framework configured to shift between a collapsed configuration and an expanded configuration, and an occlusive element disposed over an outer surface of the expandable framework. The expandable framework may include a plurality of anchor members extending radially outward from the expandable framework and through the occlusive element. At least some of the plurality of anchor members may each have two barbs projecting circumferentially therefrom.

In addition or alternatively, and in a seventeenth aspect, each barb comprises a semi-elliptical nub, each semi-elliptical nub on a particular anchor member extending in a common circumferential direction from the particular anchor member.

In addition or alternatively, and in an eighteenth aspect, the two barbs extend in opposing circumferential directions from their respective anchor member.

In addition or alternatively, and in a nineteenth aspect, a distal portion of the occlusive element is attached to the expandable framework and attachment of the distal portion of the occlusive element to the expandable framework is devoid of sutures and adhesives.

In addition or alternatively, and in a twentieth aspect, each of the plurality of anchor members has at least one barb projecting circumferentially therefrom.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
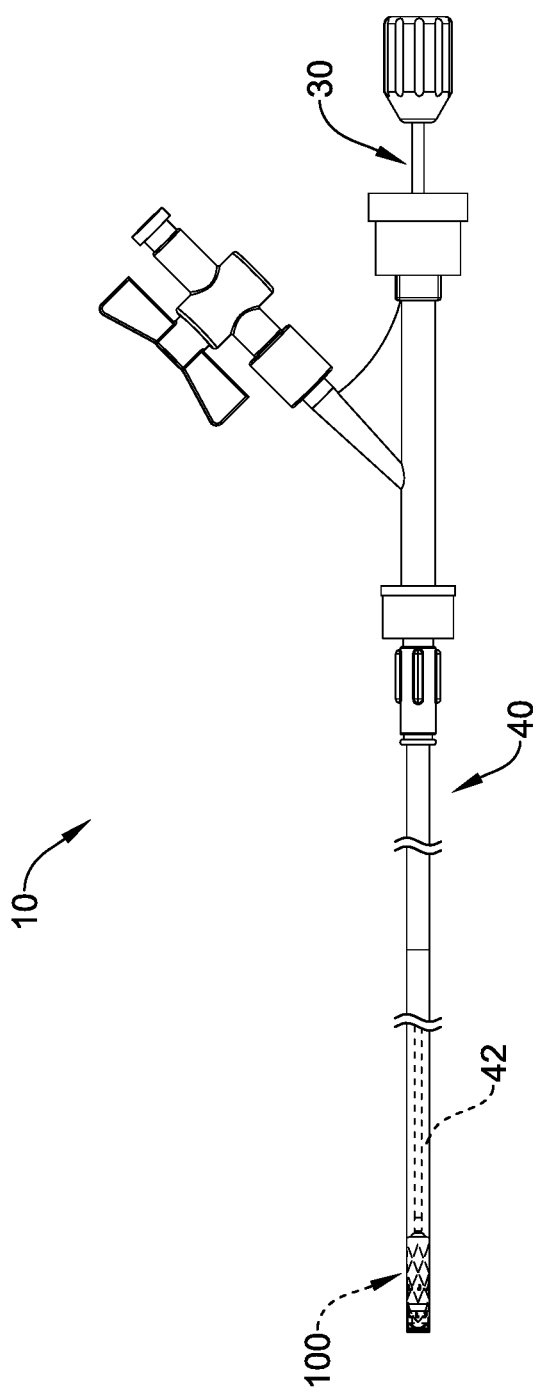
FIGS. 1-2 are side views of an example occlusive implant system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of the blood pool in the LAA. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, medical devices and/or occlusive implants have been developed that close off the left atrial appendage from the heart and/or circulatory system, thereby lowering the risk of stroke due to thrombolytic material entering the blood stream from the left atrial appendage. Additionally, to ease delivery and/or placement procedures of the medical devices and/or occlusive implants, favorable new features have been developed.

Figure 2:
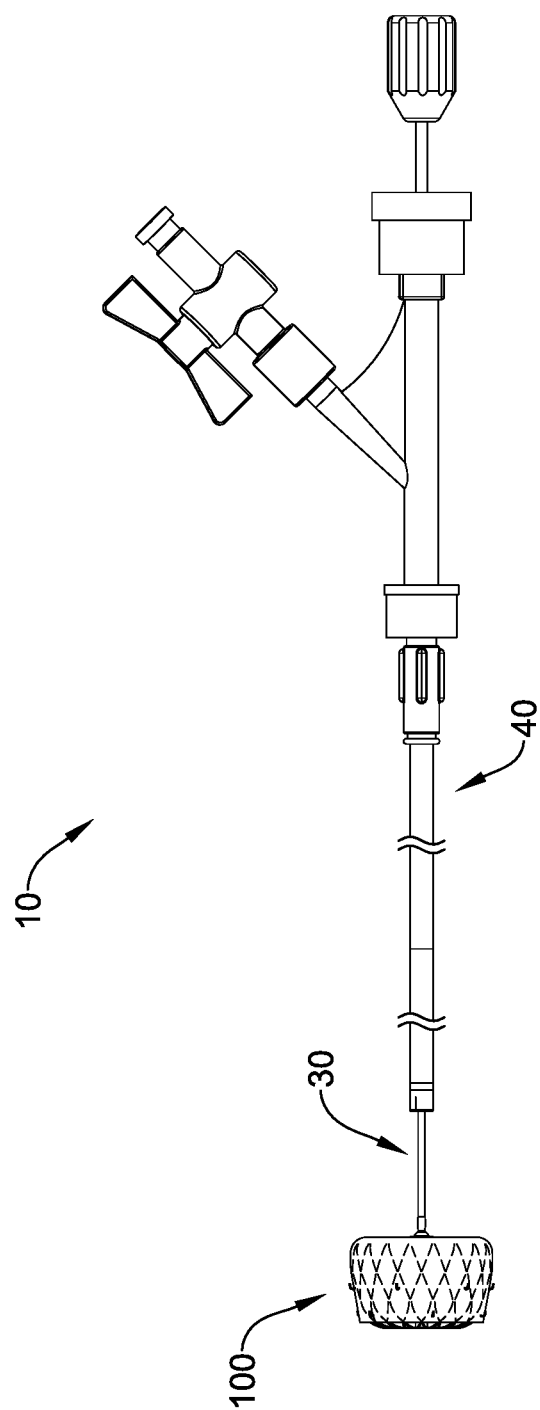
Figure 3:
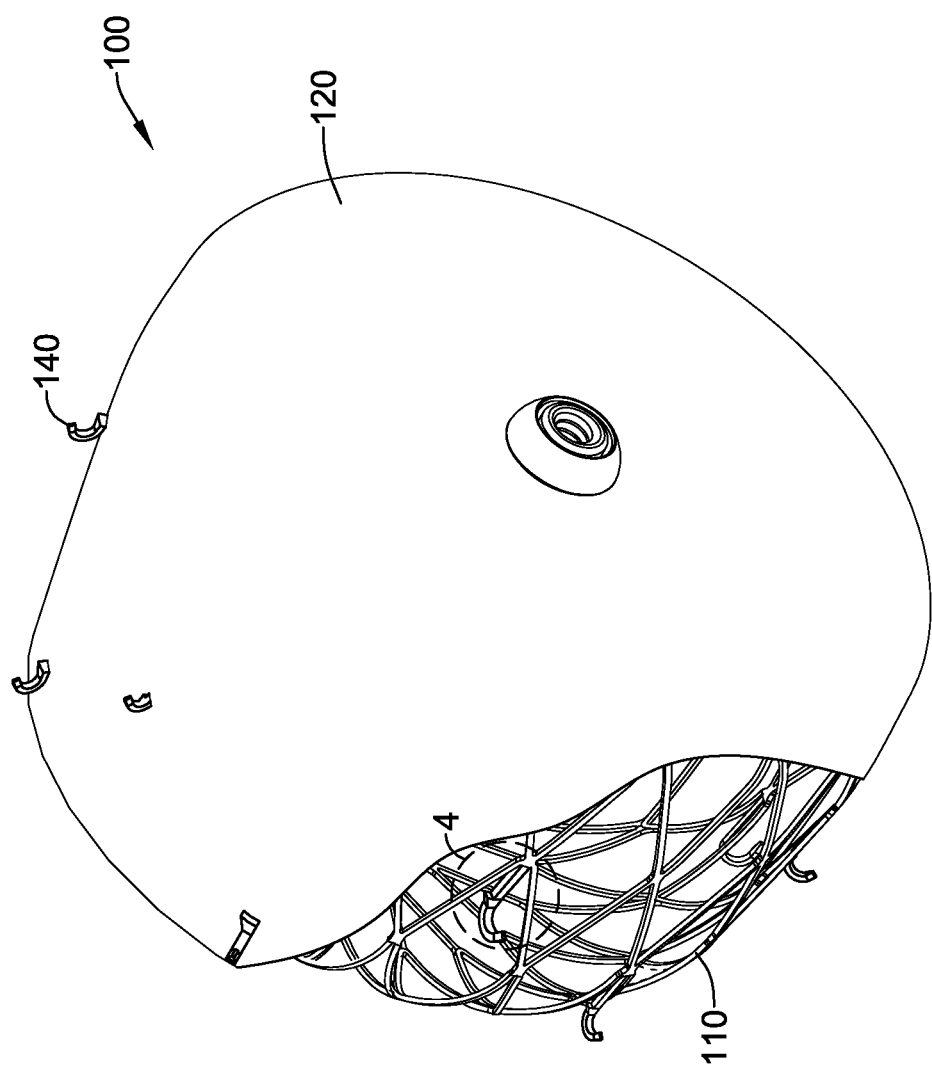
FIG. 3 is a perspective view of an example occlusive implant.

Turning now to the figures, FIGS. 1-3 illustrate an occlusive implant system 10 including a catheter 40 having a lumen 42 extending from a proximal opening to a distal opening, a core wire 30 slidably disposed within the lumen 42, and an occlusive implant 100 having an expandable framework 110 configure to shift between a collapsed configuration (e.g., FIG. 1), wherein the occlusive implant 100 is disposed within the lumen 42 proximate the distal opening in the collapsed configuration, and an expanded configuration (e.g., FIG. 2), and an occlusive element 120 disposed on the expandable framework 110 (e.g., FIG. 3), wherein the occlusive implant 100 and/or the expandable framework 110 is configured to shift between the collapsed configuration and the expanded configuration when the occlusive implant 100 is disposed distal of the distal opening of the lumen 42 and/or the catheter 40, and/or when the occlusive implant 100 is unconstrained by the catheter 40. The occlusive implant 100 may be disposed at and/or releasably connected to a distal portion of the core wire 30. The core wire 30 may be slidably and/or rotatably disposed within the lumen 42 of the catheter 40. In some embodiments, a proximal end of the core wire 30 may extend proximally of a proximal end of the catheter 40 and/or the proximal opening of the lumen 42 for manual manipulation by a clinician or practitioner. In some embodiments, the example occlusive implant 100 may be removably attached, joined, or otherwise connected to the distal end of the core wire 30. Some suitable, but non-limiting, examples of materials for the occlusive implant system 10, the core wire 30, the catheter 40, and/or the occlusive implant 100, etc. are discussed below. It is contemplated that any and/or all example occlusive implants disclosed herein may be used in accordance with and/or be associated with the example occlusive implant system 10 described above.

FIG. 3 illustrates some additional details of an example configuration of the occlusive implant 100 comprising the expandable framework 110 configured to shift between the collapsed configuration and the expanded configuration. The expandable framework 110 may be compliant and substantially conform to and/or be in sealing engagement with the shape and/or geometry of a lateral wall of a left atrial appendage in the expanded configuration. In some embodiments, the occlusive implant 100 may expand to a size, extent, or shape less than or different from a maximum unconstrained extent, as determined by the surrounding tissue and/or lateral wall of the left atrial appendage. Reducing a thickness of various elements of the expandable framework 110 may increase the flexibility and compliance of the expandable framework 110 and/or the occlusive implant 100, thereby permitting the expandable framework 110 and/or the occlusive implant 100 to conform to the tissue around it, rather than forcing the tissue to conform to the expandable framework 110 and/or the occlusive implant 100.

The occlusive implant 100 may include the occlusive element 120 disposed on, disposed over, disposed about, or covering at least a portion of the expandable framework 110. In some embodiments, the occlusive element 120 may be disposed on, disposed over, disposed about or cover at least a portion of an outer (or outwardly-facing) surface of the expandable framework 110. In some embodiments, a proximal end of the expandable framework 110 may be configured to releasably attach, join, couple, engage, or otherwise connect to the distal end of the core wire 30. In some embodiments, the proximal end of the expandable framework 110 may include a threaded insert coupled thereto. In some embodiments, the threaded insert may be configured to and/or adapted to couple with, join to, mate with, or otherwise engage a threaded member disposed at the distal end of the core wire 30. Other means of releasably coupling and/or engaging the proximal end of the expandable framework 110 to the distal end of the core wire 30 are also contemplated.

Figure 4:
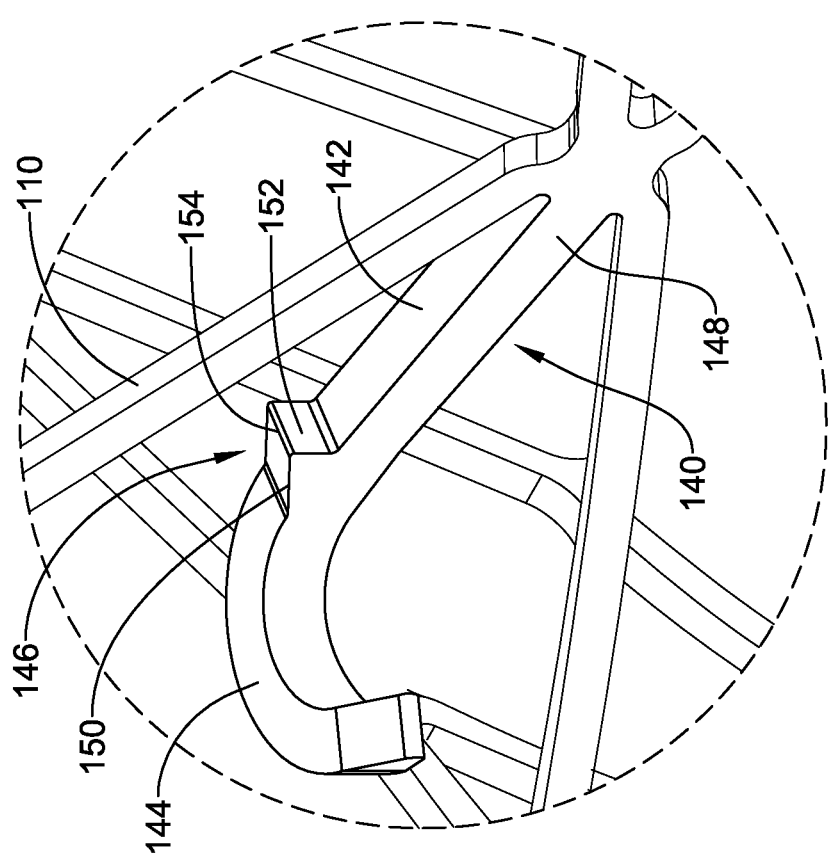
FIG. 4 illustrates an example anchor member of the occlusive implant of FIG. 3.

In some embodiments, and as seen in FIG. 3, the expandable framework 110 may include a plurality of anchor members 140 disposed about a periphery of the expandable framework 110 in the expanded configuration, an example of which may be seen in the detailed view of FIG. 4. The plurality of anchor members 140 may extend radially outward from the expandable framework 110. In some embodiments, at least some of the plurality of anchor members 140 may each have and/or include a body portion 142, a tip portion 144, and a barb 146 projecting circumferentially therefrom, as shown in FIG. 4. In some embodiments, some and/or each of the plurality of anchor members 140 have at least one barb 146 projecting circumferentially therefrom. Some suitable, but non-limiting, examples of materials for the expandable framework 110, the plurality of anchor members 140, and/or the barb(s) 146, etc. are discussed below.

The body portion 142 of each of the plurality of anchor members 140 may be attached to the expandable framework 110 at a base 148 of its respective anchor member 140. The body portion 142 of each of the plurality of anchor members 140 may extend axially distally, toward the distal end of the expandable framework 110 and/or the occlusive implant 100, and/or in a distal direction from the base 148 of the anchor member 140. The tip portion 144 of each of the plurality of anchor members 140 may be formed with a curve or hook shape such that a free end of the anchor member 140 generally extends proximally and/or toward the proximal end of the expandable framework 110 and/or the occlusive implant 100, and the base 148 of the anchor member 140 may generally be disposed proximal of the tip portion 144. In an alternative example, the tip portion 144 of each of the plurality of anchor members 140 may be formed with a generally straight or spear shape such that a free end of the anchor member 140 generally extends proximally and/or toward the proximal end of the expandable framework 110 and/or the occlusive implant 100, and the base 148 of the anchor member 140 is disposed distally of the tip portion 144.

In some embodiments, each barb 146 projecting circumferentially from at least some of the plurality of anchor members 140 projects from the body portion 142 of its respective anchor member 140. Each barb 146 may project from the body portion 142 of the anchor member 140 in a circumferential direction around the expandable framework 110 and/or a central longitudinal axis of the occlusive implant 100. In at least some embodiments, the circumferential direction may be transverse, lateral, and/or generally perpendicular to the body portion 142 and/or the tip portion 144 of the anchor member 140.

Each barb 146 may include a forward surface 150 facing towards the tip portion 144 of its respective anchor member 140, and a rear surface 152 facing towards the base 148 and/or the body portion 142 of its respective anchor member 140. The forward surface 150 may be positioned at an obtuse angle relative to the body portion 142 and/or the tip portion 144 of its respective anchor member 140. For example, the forward surface 150 may face distally and/or away from the base 148 and/or the body portion 142, as well as circumferentially relative to the body portion 142 of its respective anchor member 140 and/or the central longitudinal axis of the occlusive implant 100. In at least some embodiments, the rear surface 152 may be positioned at an obtuse angle relative to the body portion 142 of its respective anchor member 140, and the forward surface 150 and the rear surface 152 may be angled to face in a common and/or the same circumferential direction. For example, the rear surface 152 may face proximally and/or toward the base 148 and/or the body portion 142, as well as circumferentially relative to the body portion 142 of its respective anchor member 140 and/or the central longitudinal axis of the occlusive implant 100. Alternatively, in some embodiments, the rear surface 152 may be positioned at an acute angle or a right angle relative to the body portion 142 of its respective anchor member 140, and in embodiments with the acute angle, the forward surface 150 and the rear surface 152 may be angled to face in opposing circumferential directions. An intersection of the forward surface 150 with the rear surface 152 may form a barb tip 154. In at least some embodiments, the barb tip 154 may be rounded. For example, the barb tip 154 may be formed with a radius of about 0.025 inches, 0.015 inches, 0.010 inches, 0.005 inches, 0.002 inches, 0.001 inches, or another suitable dimension as desired.

In some embodiments, the plurality of anchor members 140 may provide an anchoring mechanism to aid in retaining the occlusive implant 100 at a target site within a patient's anatomy (i.e., the left atrial appendage, for example) in the expanded configuration. However, the barb(s) 146 may be configured, positioned, and/or arranged such that engagement of the barb(s) 146 with surrounding tissue at the target site is minimized or avoided. For example, the barb(s) 146 may not puncture, pierce, and/or extend into the surrounding tissue in the expanded configuration. Additionally, in some embodiments, the plurality of anchor members 140 may provide an attachment mechanism for securing the occlusive element 120 to the expandable framework 110.

Returning to FIG. 3, the occlusive element 120 may extend distally past at least some of the plurality of anchor members 140. In some embodiments, the occlusive element 120 may extend distally past each and/or all of the plurality of anchor members 140. In at least some embodiments, at least a distal portion of the occlusive element 120 may be attached to the expandable framework 110. In some embodiments, at least some of the plurality of anchor members 140 extend and/or project through the occlusive element 120. In some embodiments, each and/or all of the plurality of anchor members 140 extend and/or project through the occlusive element 120. In some embodiments, the membrane or occlusive element may be attached to the frame at some and/or each of the plurality of anchor members 140, for example, by passing some and/or each of the plurality of anchor members 140 through the occlusive element 120.

In some embodiments, the barb 146 on some and/or each of the at least some of the plurality of anchor members 140 may be disposed radially outward of the occlusive element 120 and/or exterior of the occlusive element 120 while the base of its respective anchor member 140 is disposed radially inward of and/or interior of the occlusive element 120. The barb 146 may serve to retain the occlusive element 120 on the expandable framework 110, thereby preventing the occlusive element 120 from working loose and/or releasing from the expandable framework 110 as the expandable framework 110 is shifted between the collapsed configuration and the expanded configuration. In some embodiments, attachment of the distal portion of the occlusive element 120 to the expandable framework 110 is devoid of sutures and/or adhesives.

In one example, a frame path following along an outer surface of the expandable framework 110 from the proximal end of the expandable framework 110 and/or the core wire 30 to the at least some of the plurality of anchor members 140 extending through the occlusive element 120 may be longer than an occlusive element path following along an outer surface of the occlusive element 120 from the proximal end of the expandable framework 110 and/or the core wire 30 to the at least some of the plurality of anchor members 140 extending through the occlusive element 120 when in the expanded configuration, because the outer surface of the expandable framework 110 may take a curving undulating path while the outer surface of the occlusive element 120 may take a more direct arcing path. As such, when the occlusive implant 100 and/or the expandable framework 110 is shifted to the collapsed configuration for delivery and/or disposal within the lumen 42 of the catheter 40, the occlusive element 120 may be placed in tension and/or stretched tight along the outer surface of the expandable framework 110 and/or result in a portion of the expandable framework 110 deforming and/or buckling under the tension of the occlusive element 120. The tension may be reduced by extending and/or increasing the length of the occlusive element path (e.g., making the occlusive element 120 longer) while keeping and/or maintaining the length of the frame path (e.g., not changing dimensions of the expandable framework). To accommodate the changes in tension, the occlusive element 120 may be free to move axially along the body portion 142 of the at least some of the plurality of anchor members 140 extending through the occlusive element 120. For example, the occlusive element 120 may be devoid of fixed attachment (e.g., may not be fixedly secured in place, such as with sutures or adhesives) to the plurality of anchor members 140 and/or the expandable framework 110. The barb(s) 146 may prevent the longer occlusive element 120 from slipping off the at least some of the plurality of anchor members 140 extending through the occlusive element 120 when the occlusive implant 100 and/or the expandable framework 110 is shifted to the expanded configuration and the tension is released or reduced.

In some embodiments, the occlusive element 120 may be permeable or impermeable to blood and/or other fluids, such as water. In some embodiments, the occlusive element 120 may include a polymeric membrane, a metallic or polymeric mesh, a porous filter-like material, or other suitable construction. In some embodiments, the occlusive element 120 prevents thrombi (i.e. blood clots, etc.) from passing through the occlusive element 120 and out of the left atrial appendage into the blood stream. In some embodiments, the occlusive element 120 promotes endothelization after implantation, thereby effectively removing the left atrial appendage from the patient's circulatory system. Some suitable, but non-limiting, examples of materials for the occlusive element 120 are discussed below.

Figure 5:
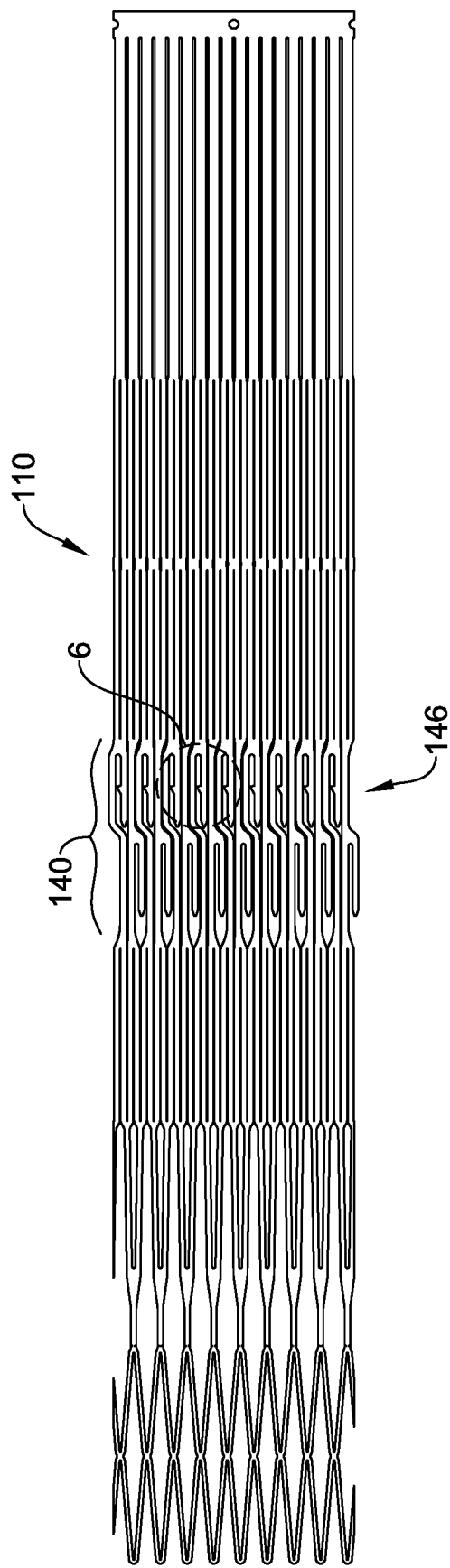
FIG. 5 is a flat pattern view of an example occlusive implant.

FIG. 5 illustrates a flat pattern corresponding to one example of the expandable framework 110 of the occlusive implant 100. The expandable framework 110 and the plurality of anchor members 140 may be integrally formed and/or cut from a unitary member. In some embodiments, the expandable framework 110 and the plurality of anchor members 140 may be integrally formed and/or cut from a unitary tubular member and subsequently formed and/or heat set to a desired shape in the expanded configuration. In some embodiments, the expandable framework 110 and the plurality of anchor members 140 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 110 include laser cutting, machining, punching, stamping, electro discharge machining (EDM), chemical dissolution, etc. Other means and/or methods are also contemplated.

Figure 5A:
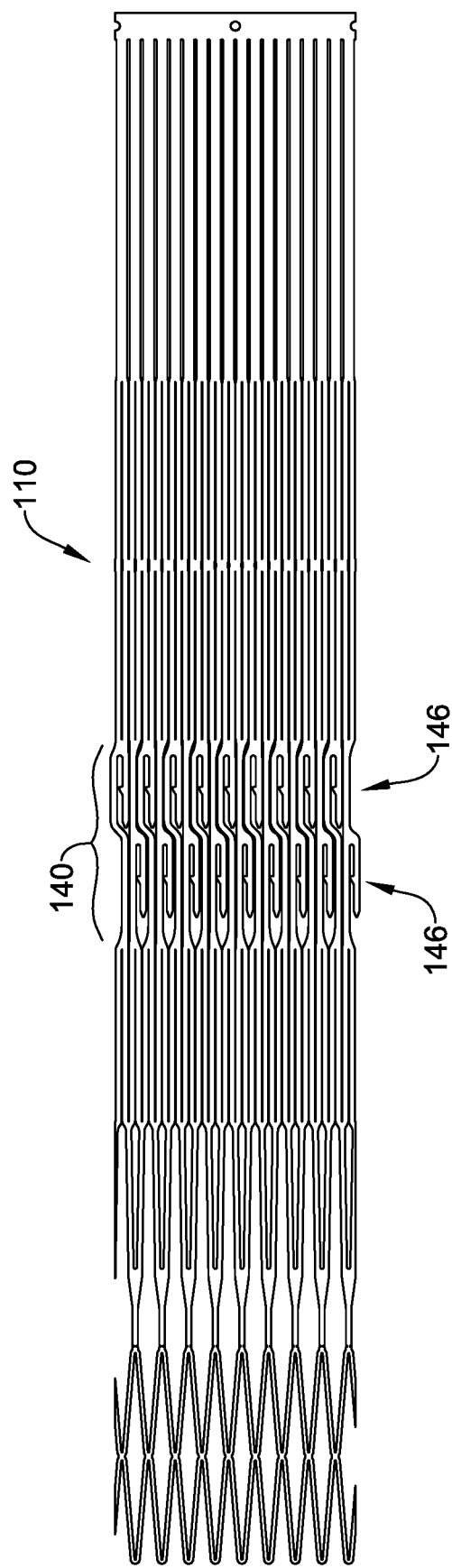
FIG. 5A is a flat pattern view of an alternative configuration of the example occlusive implant of FIG. 5.

In the example illustrated in FIG. 5, the plurality of anchor members 140 comprises two rows of anchor members 140, and one row (e.g., a proximal row) of the plurality of anchor members 140 includes the barb(s) 146. In another example, a distal row of the plurality of anchor members 140 may include the barb(s) 146. In yet another example, both rows of the plurality of anchor members 140, and/or all or each of the plurality of anchor members 140, may include the barb(s) 146, as shown in the flat pattern view of FIG. 5A. Alternatively, some (e.g., less than all) of the plurality of anchor members 140 in one or both rows of the plurality of anchor members 140 may include the barb(s) 146. Other configurations are also contemplated.

Figure 6:
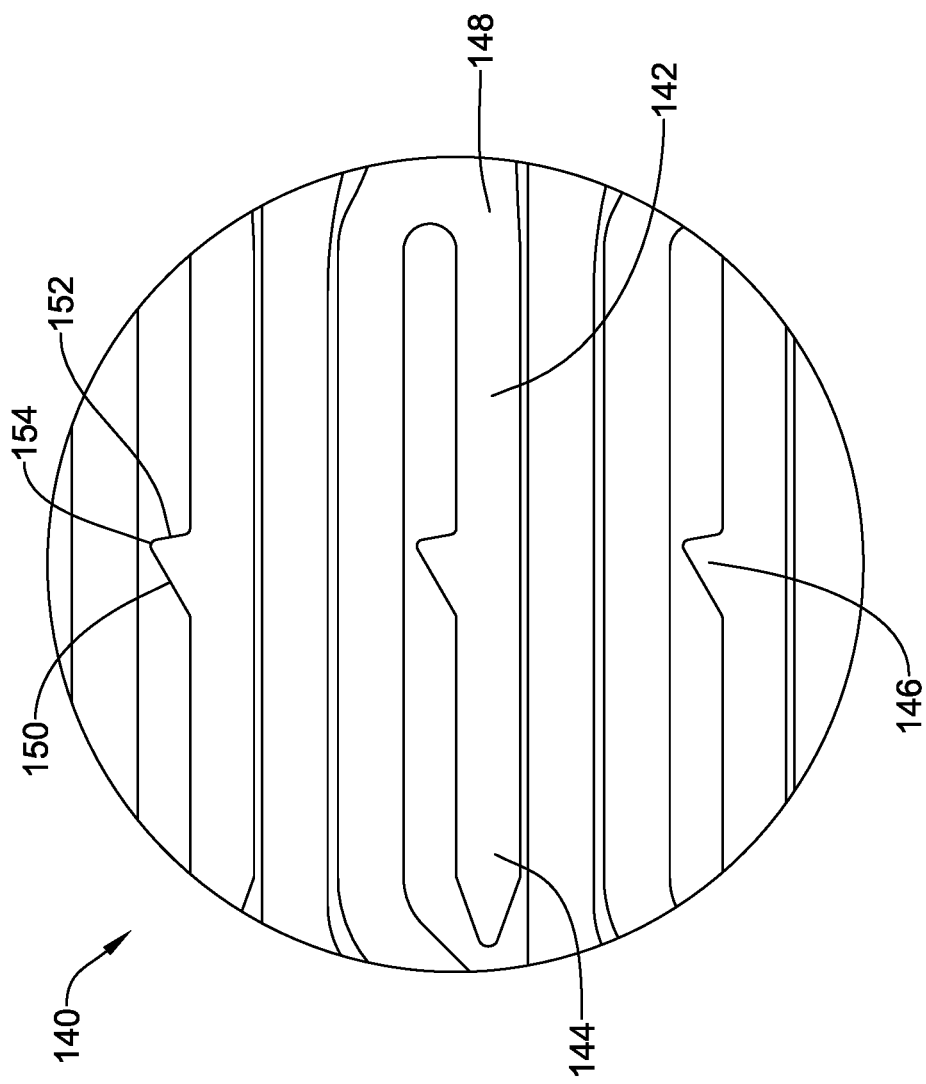
FIG. 6 is a detailed view of a portion of the flat pattern view of FIG. 5.
Figure 7:
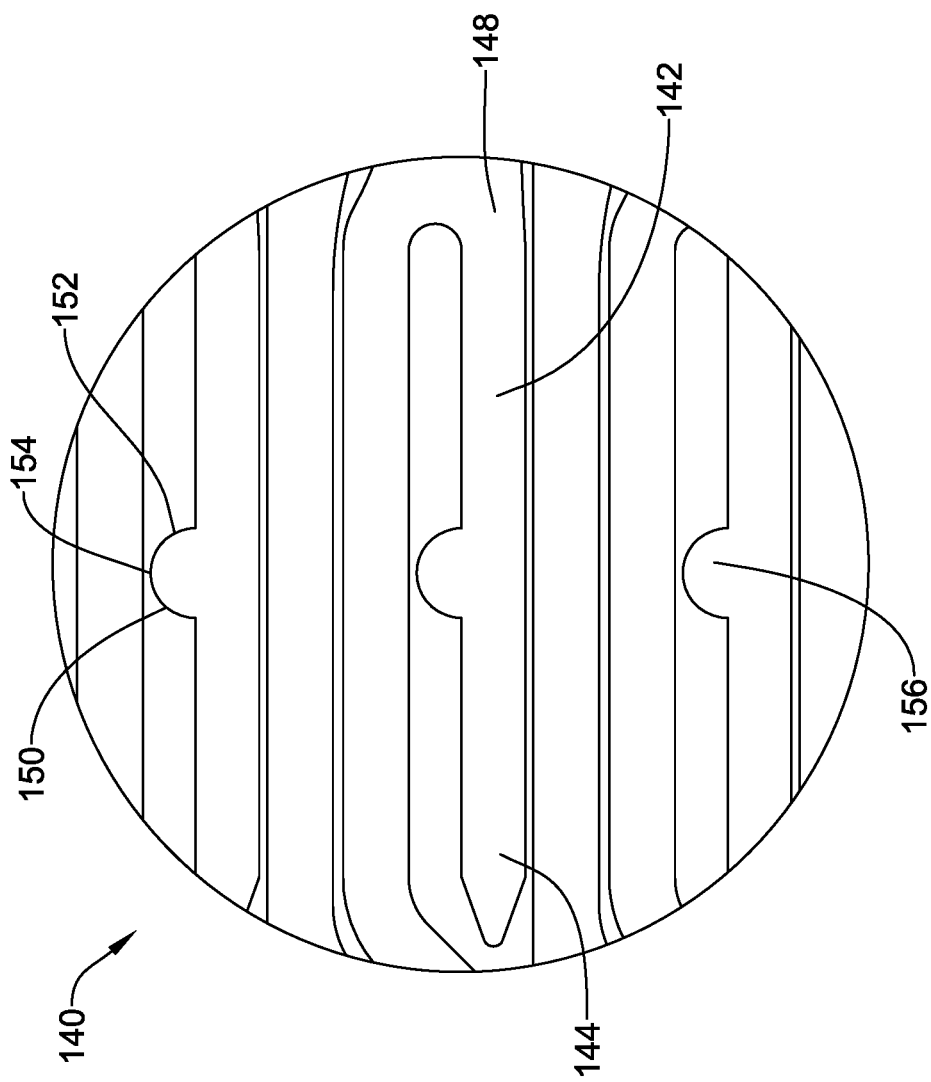
FIG. 7 illustrates an alternative configuration of the detailed view of FIG. 6.

FIG. 6 illustrates a detailed view of one example configuration of the plurality of anchor members 140 and barb(s) 146. As mentioned above, each barb 146 projects circumferentially from at least some of the plurality of anchor members 140 and may project from the body portion 142 of its respective anchor member 140. Each barb 146 may include the forward surface 150 facing towards the tip portion 144 of its respective anchor member 140, and the rear surface 152 facing towards the base 148 and/or the body portion 142 of its respective anchor member 140. In some embodiments, the forward surface 150 may be positioned and/or arranged at an obtuse angle to an axis of the body portion 142 of its respective anchor member 140. In some embodiments, the forward surface 150 may be positioned and/or arranged at an angle of about 130 to 170 degrees, about 140 to 160 degrees, about 150 degrees, etc. In some embodiments, the rear surface 152 may be positioned and/or arranged at an obtuse angle to an axis of the body portion 142 of its respective anchor member 140. In some embodiments, the rear surface 152 may be positioned and/or arranged at an angle of about 95 to 130 degrees, about 100 to 120 degrees, etc. The intersection of the forward surface 150 with the rear surface 152 may form the barb tip 154, and in at least some embodiments, the barb tip 154 may be rounded. In some embodiments, the barb(s) 146 may be configured such that the occlusive element 120 may be manually removed from the plurality of anchor members 140 by a technician or operator by manipulating the occlusive element 120 over and/or around the barb(s) 146, but the occlusive element 120 is incapable of coming off (e.g., falling off, etc.) of the plurality of anchor members 140 on its own. In an alternative example, some and/or each barb 146 may comprise a semi-elliptical nub 156, as seen in FIG. 7. Other configurations and/or arrangements are also contemplated.

Figure 8:
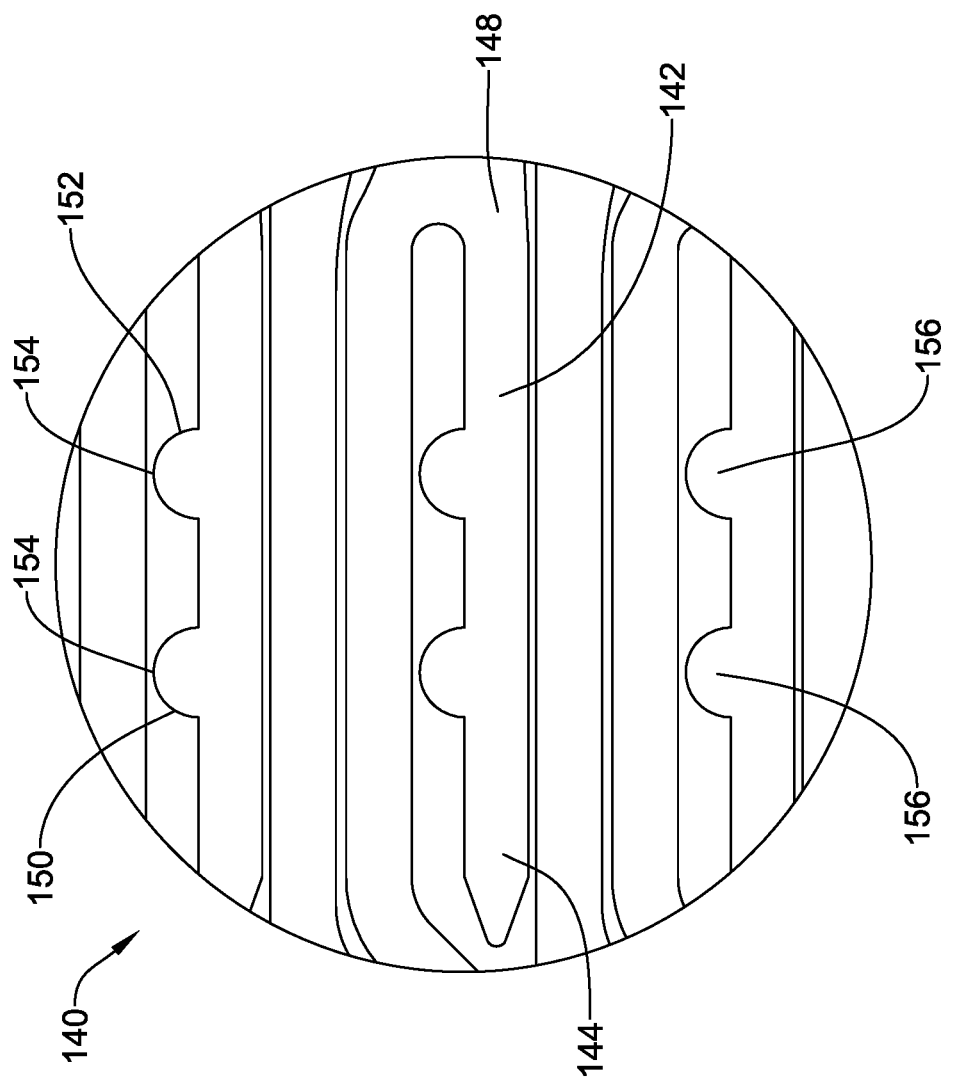
FIG. 8 illustrates an alternative configuration of the detailed view of FIG. 6.
Figure 9:
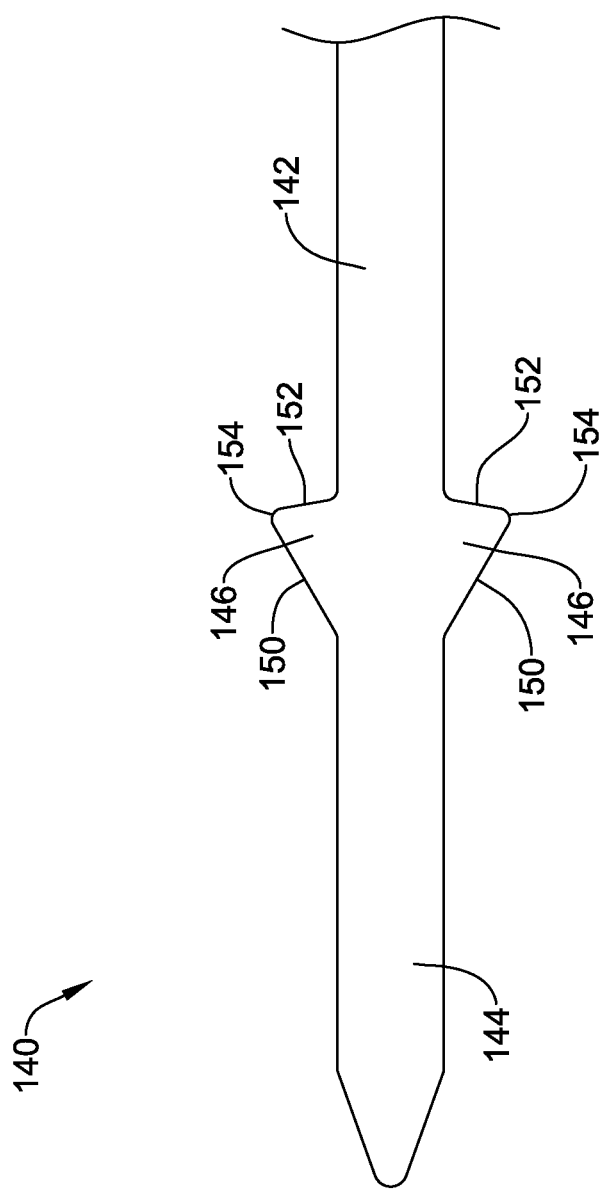
FIG. 9 illustrates an alternative configuration of the detailed view of FIG. 6.

In some embodiments, at least some of the plurality of anchor members 140 may each have two barbs 146 projecting circumferentially therefrom. In one example, each barb may comprise a semi-elliptical nub 156, wherein each semi-elliptical nub 156 on a particular anchor member 140 extends in a common circumferential direction from the particular anchor member 140, as shown in FIG. 8. In another example, shown in FIG. 9, the two barbs 146 may extend in opposing circumferential directions from their respective anchor member 140 as substantially mirror images of each other in an "arrowhead" configuration, wherein each barb may include the forward surface 150 facing towards the tip portion 144 of its respective anchor member 140, and the rear surface 152 facing towards the base 148 (not shown, see FIG. 6) and/or the body portion 142 of its respective anchor member 140, as described above. In another alternative example, each of the two barbs 146 may be semi-elliptical nubs extending in opposing circumferential directions from their respective anchor member 140. In yet another alternative example, each of the plurality of anchor members 140 may be formed with an undulating S-curve or zigzagging shape forming a plurality of projections extending transverse to the axis of the anchor member 140. The plurality of projections could be formed in a radial direction relative to the central longitudinal axis of the occlusive implant 100, a circumferential direction relative to the central longitudinal axis of the occlusive implant 100, both radial and circumferential directions relative to the central longitudinal axis of the occlusive implant 100, or in other configurations. Other configurations and/or arrangements are also contemplated.

Figure 10:
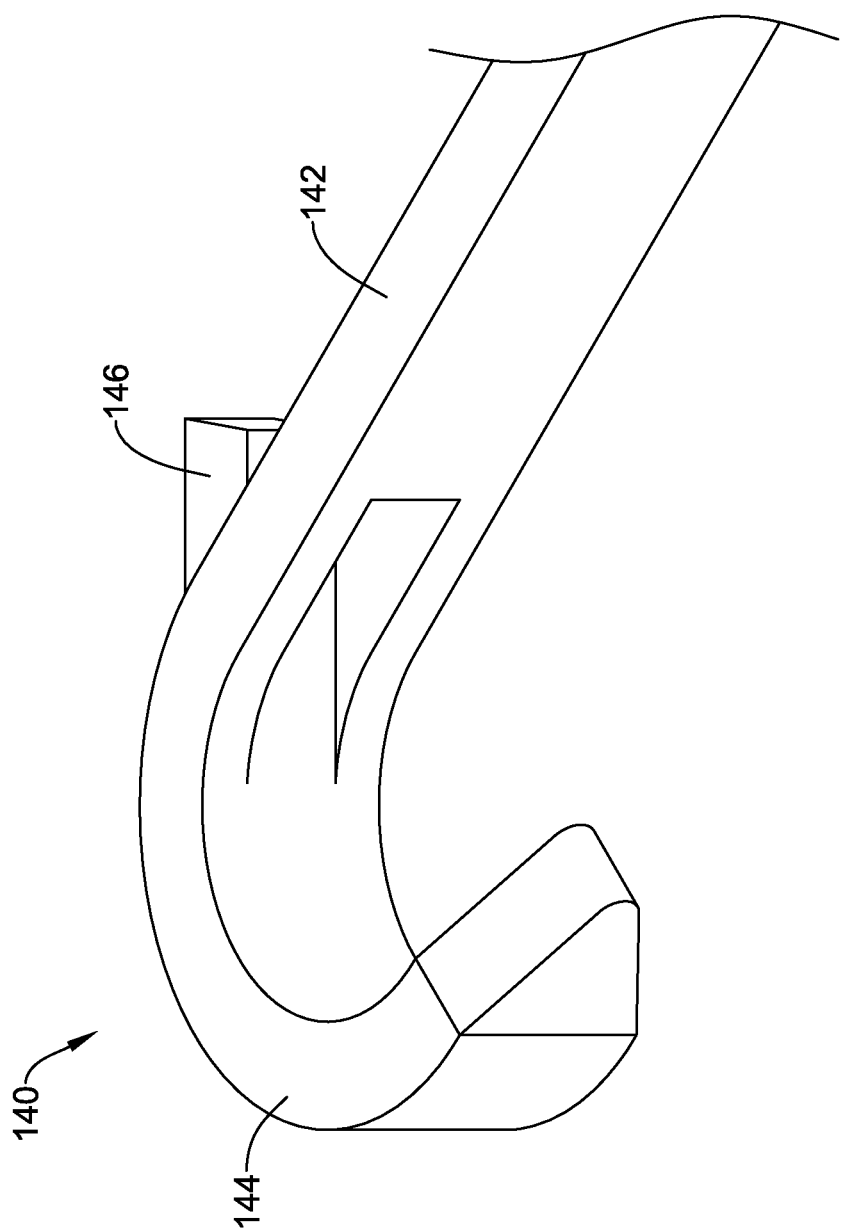
FIGS. 10 and 11 illustrate alternative configurations of an anchor member for use with the occlusive implant of FIG. 3.
Figure 11:
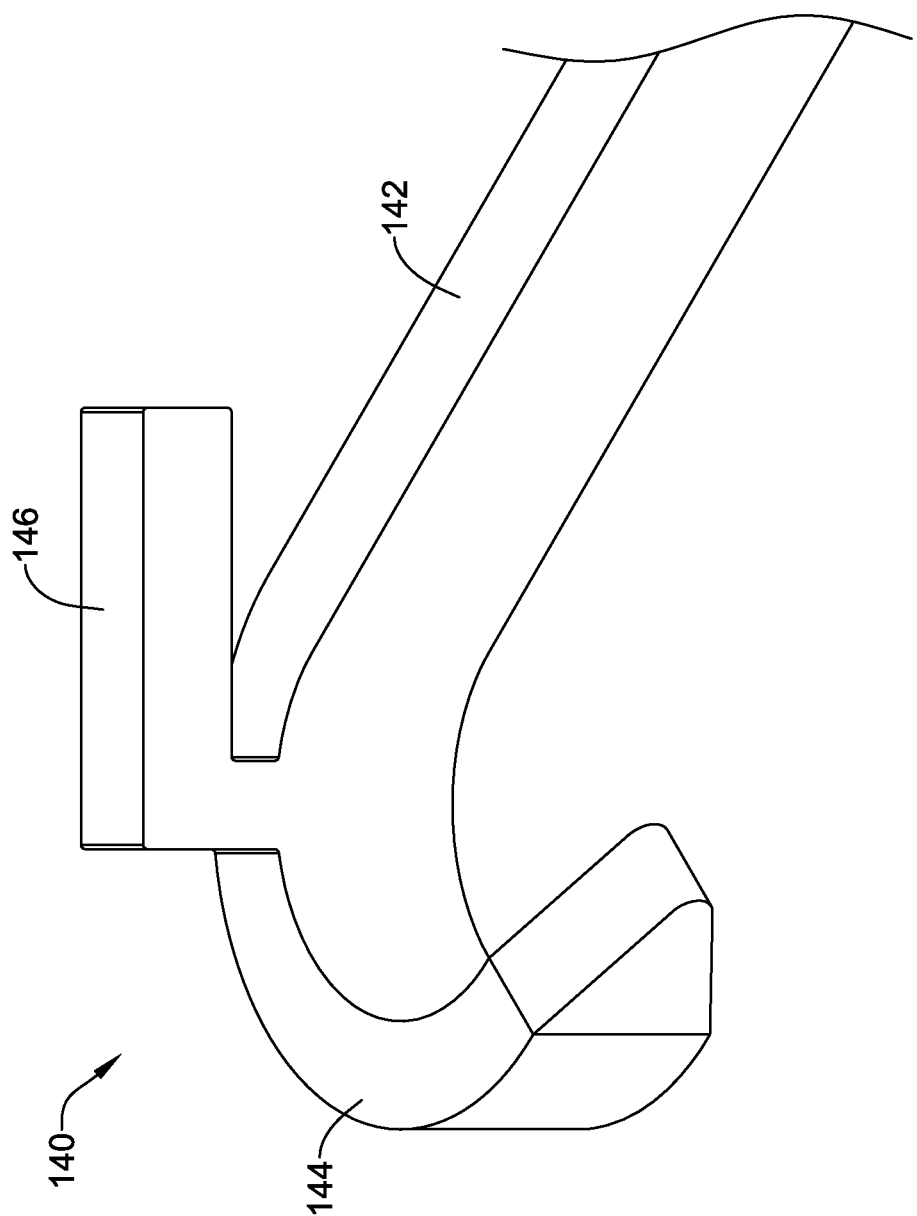

FIGS. 10 and 11 illustrate alternative examples of the plurality of anchor members 140 and/or the barb(s) 146 projecting therefrom. The barb 146 may project radially (e.g., in a radial direction, radially outward, radially inward, etc.) and/or axially from the body portion 142 and/or the tip portion 144 of its respective anchor member 140 with respect to the central longitudinal axis of the occlusive implant 100. In some embodiments, the barb 146 may project both circumferentially and radially from the body portion 142 and/or the tip portion 144 with respect to the central longitudinal axis of the occlusive implant 100. In some embodiments, the barb 146 may be formed from within a part of the body portion 142 and/or the tip portion 144 of its respective anchor member 140. For example, a profile of the barb 146 may be cut within the body portion 142 and/or the tip portion 144 such that when the anchor member 140 is formed into the curve or hook shape, or other suitable shape, the outline projects radially therefrom to form the barb 146. In some embodiments, a distal tip of the barb 146 may project radially inward toward the central longitudinal axis of the occlusive implant 100 and axially toward the proximal end of the occlusive implant 100. Other configurations and/or arrangements are also contemplated.

The materials that can be used for the various components of the occlusive implant system 10, the core wire 30, the catheter 40, the occlusive implant 100, the expandable framework 110, the occlusive element 120, the plurality of anchor members 140, etc. (and/or other systems or components disclosed herein) and the various elements thereof disclosed herein may include those commonly associated with medical devices. For simplicity purposes, the following discussion makes reference to the occlusive implant system 10, the core wire 30, the catheter 40, the occlusive implant 100, the expandable framework 110, the occlusive element 120, the plurality of anchor members 140, etc. However, this is not intended to limit the devices and methods described herein, as the discussion may be applied to other elements, members, components, or devices disclosed herein, such as, but not limited to, the body portion 142, the tip portion 144, the barb 146, the base 148, the forward surface 150, the rear surface 152, the barb tip 154, etc. and/or elements or components thereof.

In some embodiments, the occlusive implant system 10, the core wire 30, the catheter 40, the occlusive implant 100, the expandable framework 110, the occlusive element 120, the plurality of anchor members 140, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-superelastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant system 10, the core wire 30, the catheter 40, the occlusive implant 100, the expandable framework 110, the occlusive element 120, the plurality of anchor members 140, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant system 10, the core wire 30, the catheter 40, the occlusive implant 100, the expandable framework 110, the occlusive element 120, the plurality of anchor members 140, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant system 10, the core wire 30, the catheter 40, the occlusive implant 100, the expandable framework 110, the occlusive element 120, the plurality of anchor members 140, etc. to achieve the same result.

In some embodiments, a degree of Magnetic Resonance Imaging (MM) compatibility is imparted into the occlusive implant system 10, the core wire 30, the catheter 40, the occlusive implant 100, the expandable framework 110, the occlusive element 120, the plurality of anchor members 140, etc. For example, the occlusive implant system 10, the core wire 30, the catheter 40, the occlusive implant 100, the expandable framework 110, the occlusive element 120, the plurality of anchor members 140, etc., and/or components or portions thereof, may be made of a material that does not substantially distort the image and create substantial artifacts (e.g., gaps in the image). Certain ferromagnetic materials, for example, may not be suitable because they may create artifacts in an MM image. The occlusive implant system 10, the core wire 30, the catheter 40, the occlusive implant 100, the expandable framework 110, the occlusive element 120, the plurality of anchor members 140, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N®️ and the like), nitinol, and the like, and others.

In some embodiments, the occlusive implant system 10, the core wire 30, the catheter 40, the occlusive implant 100, the expandable framework 110, the occlusive element 120, the plurality of anchor members 140, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant system 10, the core wire 30, the catheter 40, the occlusive implant 100, the expandable framework 110, the occlusive element 120, the plurality of anchor members 140, etc. may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant system 10, the core wire 30, the catheter 40, the occlusive implant 100, the expandable framework 110, the occlusive element 120, the plurality of anchor members 140, etc. may include and/or be treated with a suitable therapeutic agent. Some examples of suitable therapeutic agents may include antithrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An occlusive implant, comprising:
an expandable framework configured to shift between a collapsed configuration and an expanded configuration that is configured to conform to and to be in a sealing engagement with a lateral wall of a left atrial appendage; and
an occlusive element disposed on the expandable framework;
wherein the expandable framework includes a plurality of anchor members extending radially outward from the expandable framework and through the occlusive element,
wherein each of the plurality of anchor members includes a proximal body portion and a distal tip portion that is adapted to engage tissue,
wherein at least some of the plurality of anchor members each have a barb that projects circumferentially from the at least some of the plurality of anchor members at points proximal of their respective tip portions and distal of the occlusive element and is configured to secure the occlusive element to the expandable framework.

2. The occlusive implant of claim 1, wherein the body portion of each anchor member of the at least some of the plurality of anchor members is attached to the expandable framework at a base of its respective anchor member.

3. The occlusive implant of claim 2, wherein each barb includes a forward surface facing towards the tip portion of its respective anchor member, and a rear surface facing towards the base of its respective anchor member.

4. The occlusive implant of claim 3, wherein the rear surface is positioned at an obtuse angle to the body portion.

5. The occlusive implant of claim 3, wherein the forward surface is positioned at an obtuse angle to the body portion.

6. The occlusive implant of claim 3, wherein an intersection of the forward surface with the rear surface forms a barb tip, the barb tip being rounded.

7. The occlusive implant of claim 1, wherein each barb comprises a semi-elliptical nub.

8. The occlusive implant of claim 1, wherein the expandable framework and the plurality of anchor members are formed from a unitary tubular member.

9. An occlusive implant system, comprising:
a catheter having a lumen extending from a proximal opening to a distal opening;
a core wire slidably disposed within the lumen; and
an occlusive implant having an expandable framework configured to shift between a collapsed configuration and an expanded configuration that is configured to conform to and to be in a sealing engagement with a lateral wall of a left atrial appendage, and an occlusive element disposed on the expandable framework;
wherein the expandable framework includes a plurality of anchor members extending radially outward from the expandable framework, and through the occlusive element, the plurality of anchor members each having a distal tip and a proximal body,
wherein at least some anchor members of the plurality of anchor members are configured to secure the occlusive element to the expandable framework and each of the at least some of the plurality of anchor members have a barb that projects circumferentially therefrom at a point proximal of the distal tip and distal of the occlusive element;
wherein the occlusive implant is releasably connected to a distal portion of the core wire.

10. The occlusive implant system of claim 9, wherein the occlusive implant is disposed within the lumen proximate the distal opening in the collapsed configuration.

11. The occlusive implant system of claim 9, wherein a tip portion of each of the plurality of anchor members extends towards a proximal end of the occlusive implant.

12. The occlusive implant system of claim 9, wherein the occlusive element extends distally past all of the plurality of anchor members.

13. The occlusive implant system of claim 9, wherein the plurality of anchor members each extend through the occlusive element.

14. An occlusive implant, comprising:
an expandable framework configured to shift between a collapsed configuration and an expanded configuration that is configured to conform to and to be in a sealing engagement with a lateral wall of a left atrial appendage; and
an occlusive element disposed over an outer surface of the expandable framework;
wherein the expandable framework includes a plurality of anchor members extending radially outward from the expandable framework and through the occlusive element;
wherein at least some of the plurality of anchor members each have two barbs projecting circumferentially therefrom at points distal of the occlusive element and proximal of a distal tip of the at least some of the plurality of anchor members and are configured to secure the occlusive element to the expandable framework.

15. The occlusive implant of claim 14, wherein each barb comprises a semi-elliptical nub, each semi-elliptical nub on a particular anchor member extending in a common circumferential direction from the particular anchor member.

16. The occlusive implant of claim 14, wherein the two barbs extend in opposing circumferential directions from their respective anchor member.

17. The occlusive implant of claim 14, wherein a distal portion of the occlusive element is attached to the expandable framework and attachment of the distal portion of the occlusive element to the expandable framework is devoid of sutures and adhesives.

18. The occlusive implant of claim 14, wherein each of the plurality of anchor members has at least one barb projecting circumferentially therefrom.

* * * * *